US011052186B2

(12) United States Patent
Bonnefond et al.

(10) Patent No.: US 11,052,186 B2
(45) Date of Patent: Jul. 6, 2021

(54) MEDICAL DEVICE INCLUDING A PACKAGE AND A PRE-FILLED SYRINGE DISPOSED IN THE PACKAGE

(71) Applicant: LABORATOIRE AGUETTANT, Lyons (FR)

(72) Inventors: Guillaume Bonnefond, Saint Genis Laval (FR); Vincent Guyot, Corbas (FR); Philippe Laurent, Oullins (FR)

(73) Assignee: LABORATOIRE AGUETTANT, Lyons (FR)

( * ) Notice: Subject to any disclaimer, the term of this patent is extended or adjusted under 35 U.S.C. 154(b) by 146 days.

(21) Appl. No.: 16/317,396

(22) PCT Filed: Jun. 27, 2017

(86) PCT No.: PCT/FR2017/051705
§ 371 (c)(1),
(2) Date: Jan. 11, 2019

(87) PCT Pub. No.: WO2018/011485
PCT Pub. Date: Jan. 18, 2018

(65) Prior Publication Data
US 2019/0224405 A1    Jul. 25, 2019

(30) Foreign Application Priority Data

Jul. 13, 2016 (FR) .................... 16/56712

(51) Int. Cl.
*A61M 5/00* (2006.01)
*A61M 5/315* (2006.01)
*A61M 5/32* (2006.01)

(52) U.S. Cl.
CPC ........ *A61M 5/002* (2013.01); *A61M 5/31501* (2013.01); *A61M 5/31513* (2013.01);
(Continued)

(58) Field of Classification Search
CPC .... A61M 5/002; A61M 5/008; A61M 5/3146; A61M 5/3202; A61M 5/315;
(Continued)

(56) References Cited

U.S. PATENT DOCUMENTS

| 2,421,495 A | 6/1947 | Green |
| 4,973,318 A | 11/1990 | Holm et al. |

(Continued)

FOREIGN PATENT DOCUMENTS

| CN | 202909103 A | 5/2013 |
| DK | 166948 A | 8/1993 |

(Continued)

OTHER PUBLICATIONS

International Search Report for Application No. PCT/FR2017/051705.

(Continued)

*Primary Examiner* — Nathan R Price
*Assistant Examiner* — Anna E Goldberg-Richmeier
(74) *Attorney, Agent, or Firm* — Cantor Colburn LLP

(57) ABSTRACT

This medical device (2) comprises a pre-filled syringe (3) comprising a syringe body (4) and a piston (16) mounted sliding in the syringe body (4), the syringe body (4) and the piston (16) delimiting an internal chamber (17) containing a fluid to be administered; and a package (21) in which the pre-filled syringe (3) is arranged, the package (21) comprising first and second package portions (22, 23) mounted movable relative to each other between a storage configuration in which the first and second package portions (22, 23) prevent the pre-filled syringe (4) from being removed from the package (21), and an open configuration in which the first and second package portions (22, 23) allow the pre-filled syringe (3) to be removed from the package (21), a movement of the first and second package portions (22, 23)

(Continued)

from the storage configuration to the open configuration causing the piston (16) to move from a first piston position to a second piston position.

21 Claims, 6 Drawing Sheets

(52) U.S. Cl.
CPC .... *A61M 5/31535* (2013.01); *A61M 5/31543* (2013.01); *A61M 5/3202* (2013.01)

(58) Field of Classification Search
CPC .......... A61M 5/31501; A61M 5/31513; A61M 2005/2073; A61M 2005/312; A61M 2005/3117; A61J 1/00; A61J 1/05; B65D 83/0022; B65D 83/0083; B65D 85/28
See application file for complete search history.

(56) References Cited

U.S. PATENT DOCUMENTS

| | | | |
|---|---|---|---|
| 5,417,326 A | 5/1995 | Winer | |
| 8,118,788 B2 * | 2/2012 | Frezza | A61M 5/5086 604/200 |
| 8,770,409 B2 * | 7/2014 | Cude | A61M 5/002 206/557 |
| 9,248,229 B2 * | 2/2016 | Devouassoux | A61M 5/002 |
| 2004/0024353 A1 | 2/2004 | Petersen et al. | |
| 2008/0110917 A1 | 5/2008 | Kendall et al. | |
| 2015/0297833 A1 * | 10/2015 | Henderson | A61M 5/3129 604/135 |
| 2018/0085515 A1 * | 3/2018 | Mide | B65D 75/326 |
| 2019/0083701 A1 * | 3/2019 | Bode | A61M 5/1452 |

FOREIGN PATENT DOCUMENTS

| | | |
|---|---|---|
| EP | 0327910 B1 | 4/1992 |
| FR | 2896168 | 7/2007 |
| WO | 2012076510 A1 | 6/2012 |

OTHER PUBLICATIONS

CN First Office Action for Application No. 201780043141.3.
CN Search Report for Application No. 2017800431413.
English Translation to CN First Office Action for Application No. 201780043141.3.

* cited by examiner

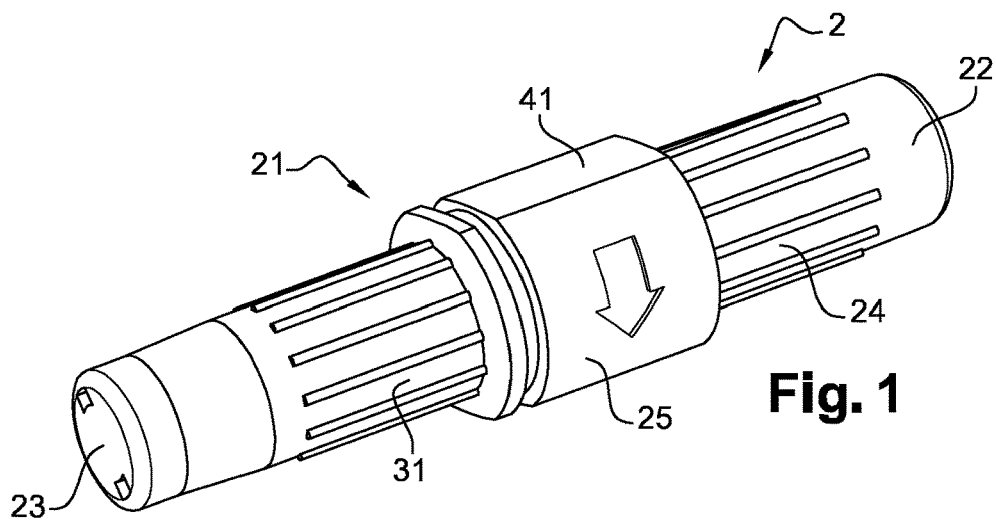
Fig. 1
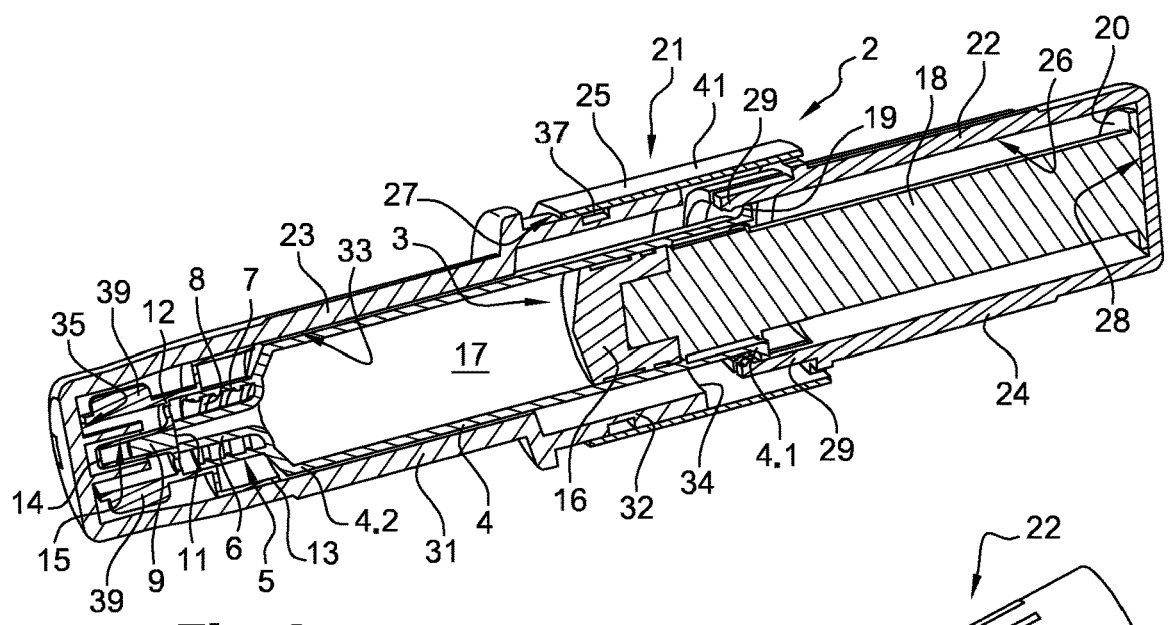
Fig. 2
Fig. 3

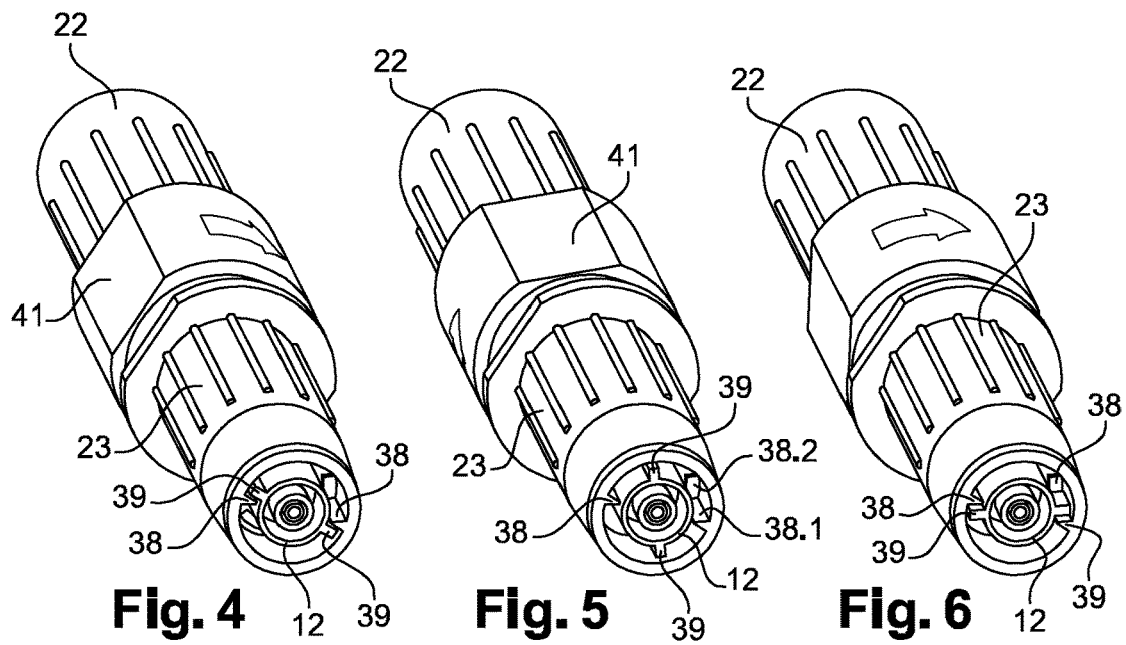
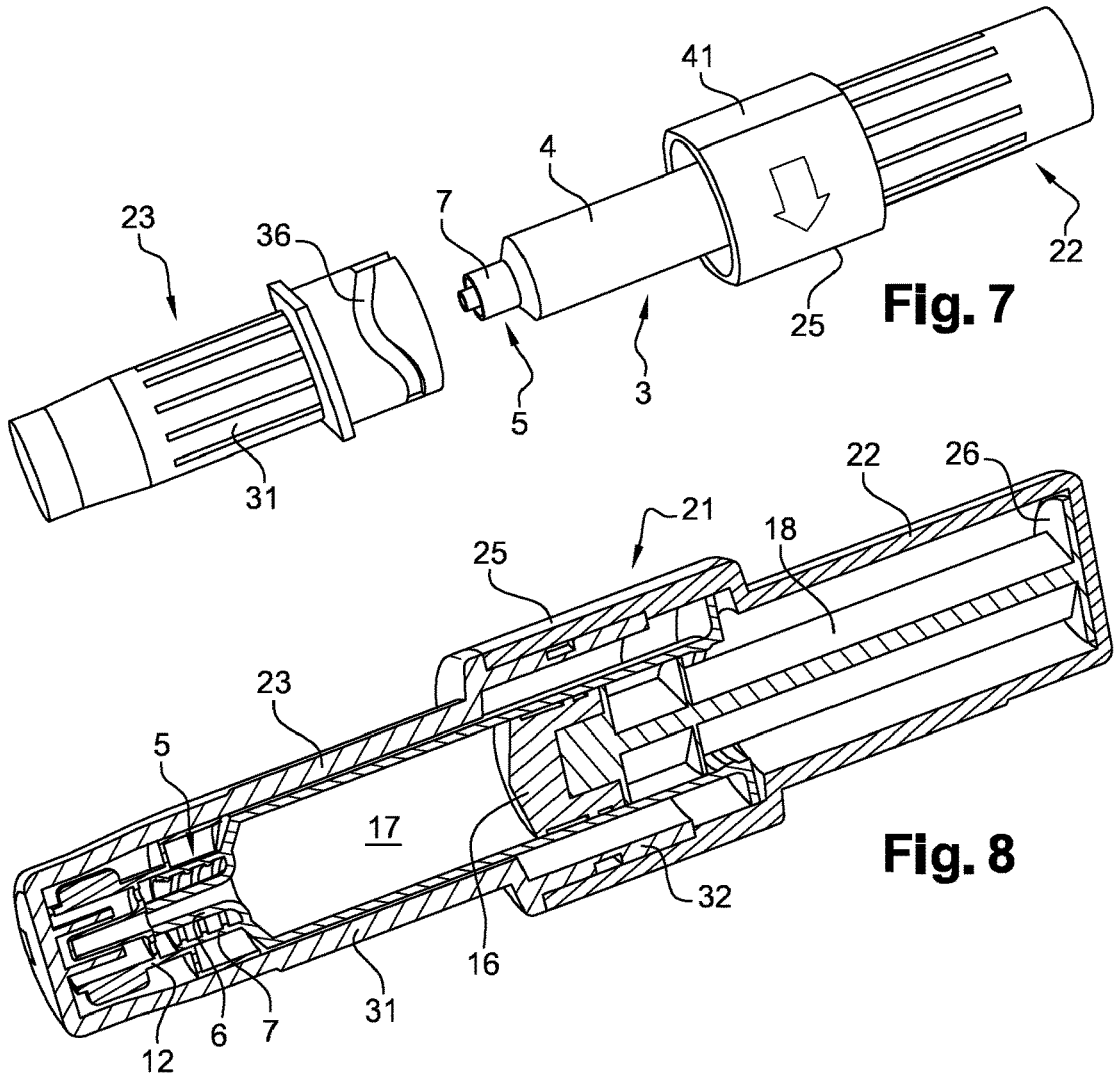

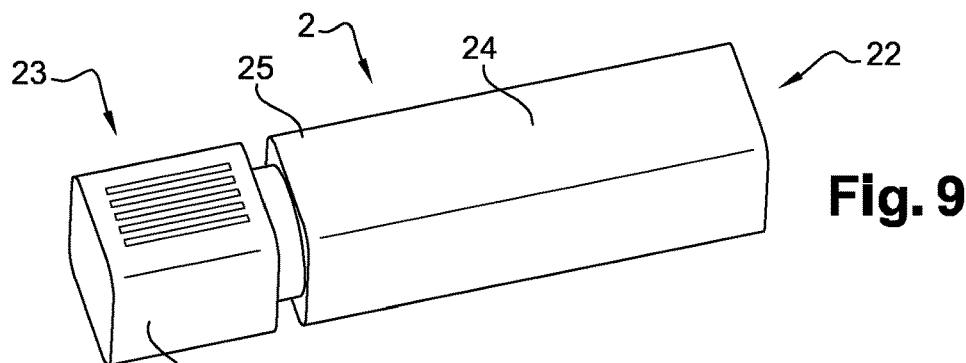
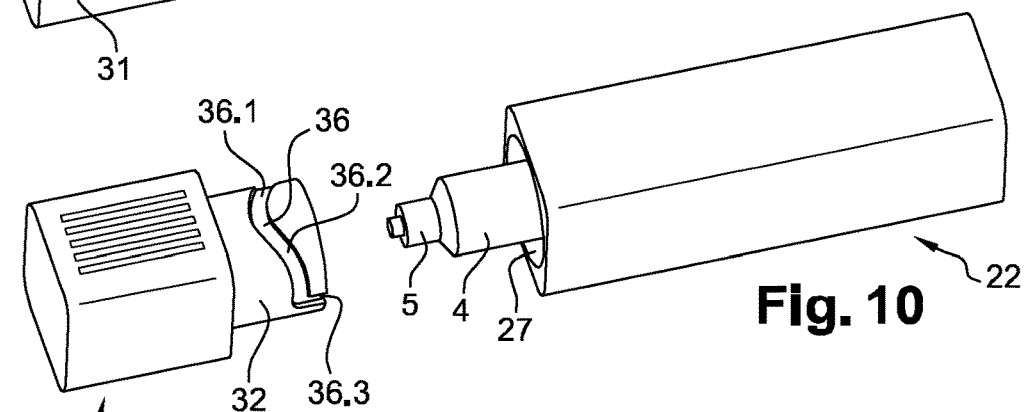
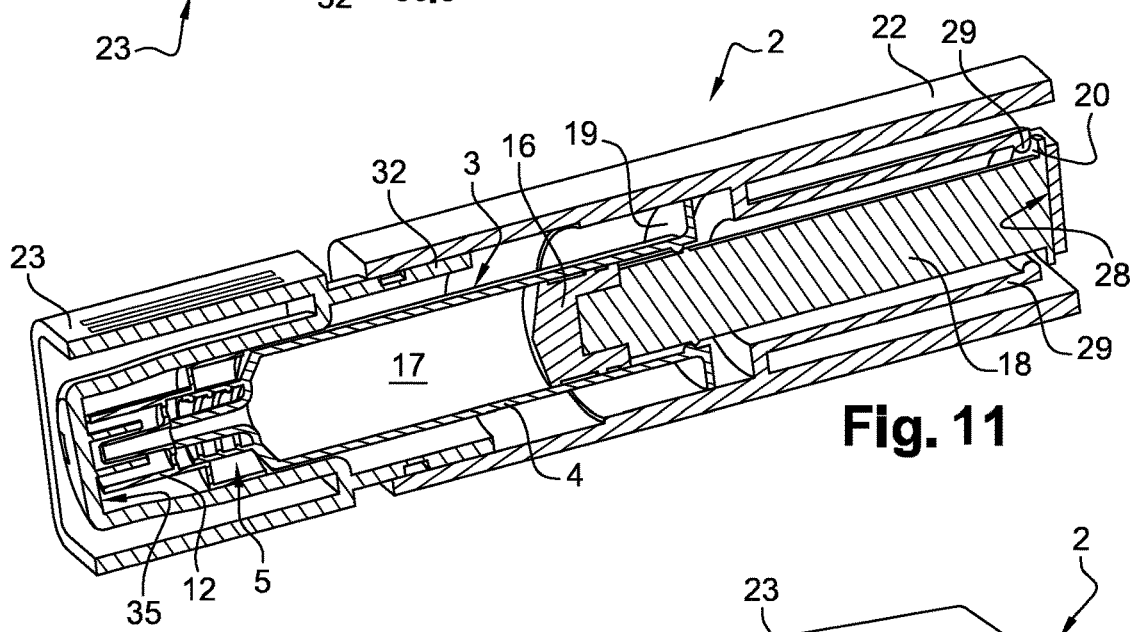
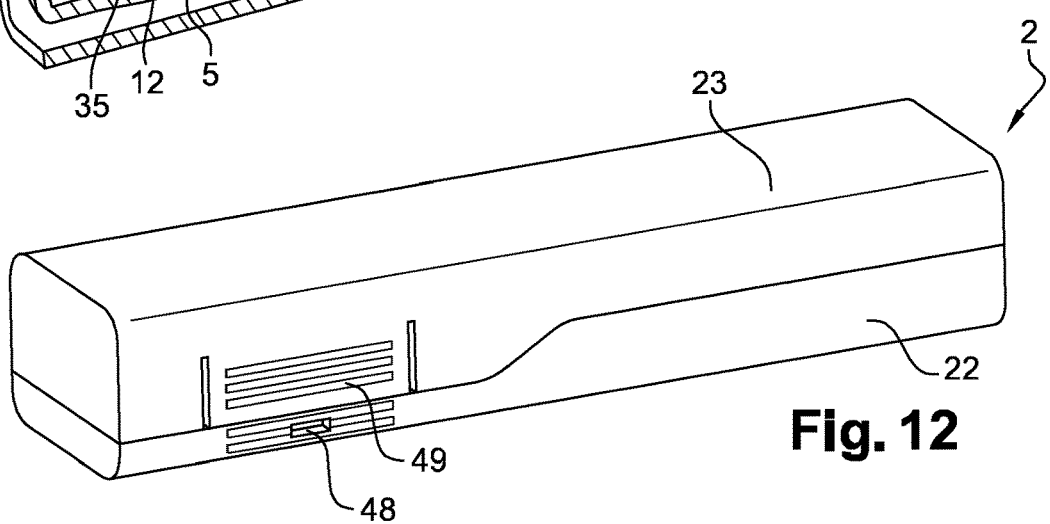

US 11,052,186 B2

MEDICAL DEVICE INCLUDING A PACKAGE AND A PRE-FILLED SYRINGE DISPOSED IN THE PACKAGE

CROSS REFERENCE TO RELATED APPLICATIONS

This application is a National Stage of PCT Application No. PCT/FR2017/051705 filed on Jun. 27, 2017, which claims priority to French Patent Application No. 16/56712 filed on Jul. 13, 2016, the contents each of which are incorporated herein by reference thereto.

TECHNICAL FIELD

The present invention concerns to a medical device including a pre-filled syringe and a package in which the pre-filled syringe is disposed.

BACKGROUND

The document FR2896168 discloses a pre-filled syringe including:
- a syringe body partially delimiting an inner chamber containing a fluid to be administered to a patient,
- a piston slidably mounted in the syringe body in an axial direction of displacement,
- a piston rod secured in translation with the piston,
- a connecting tip including a tubular connecting portion intended for the passage of the fluid to be administered,
- a obturator closing the free end of the tubular connecting portion, the obturator being connected to the free end of the tubular connecting portion by a frangible zone, and
- a protective cap mounted on the connecting tip and including a coupling portion coupled to the obturator such that a rotation of the coupling portion about an axis of rotation parallel to the extension direction of the tubular connecting portion causes a breakage of the frangible zone.

Such a pre-filled syringe is generally disposed in a package, also called blister, in order to preserve the sterility of the pre-filled syringe.

When such a pre-filled syringe is stored for a long time before its use, the piston often adheres to the inner surface of the syringe body. It is then necessary, for a practitioner wishing to administer the fluid contained in the pre-filled syringe, to actuate the piston rod prior to the breakage of the obturator in order to displace the piston within the syringe body, and therefore to «peel» it from the syringe body. Such a step constitutes a step of activating the pre-filled syringe.

However, when a practitioner forgets to perform the activation step prior to the breakage of the obturator and the removal of the protective cap, and therefore carries it out after the connection of the pre-filled syringe to the catheter connected to the patient, the application of a high pressure on the piston rod to peel the piston induces a sudden and uncontrolled displacement of the piston, and is therefore likely to cause, on the one hand, a painful administration of the fluid to be administered, and on the other hand, the administration of an amount of fluid different from that required, which could be very harmful, or even fatal, for the patient depending on the nature of the fluid to be administered.

Furthermore, when a practitioner performs the activation step after the breakage of the obturator and the removal of the protective cap, but before the connection of the pre-filled syringe to the catheter connected to the patient, the application of a high pressure on the piston rod to peel the piston induces a sudden ejection of an amount of the fluid to be administrated out of the syringe, and therefore a loss of product and a risk for the practitioner or the patient to be contaminated by the ejected fluid.

BRIEF SUMMARY

The present invention aims at overcoming these drawbacks.

The technical problem underlying the invention therefore consists in providing a medical device including a pre-filled syringe, which ensures a reliable, safe and non-dangerous administration of the fluid to be administered contained in the pre-filled syringe, and which participates in limiting the errors and risks of use by healthcare professionals.

To this end, the present invention concerns a medical device, comprising:
- a pre-filled syringe including a syringe body and a piston slidably mounted in the syringe body in an axial direction of displacement, the syringe body and the piston delimiting an inner chamber containing a fluid to be administered to a patient; and
- a package in which the pre-filled syringe is disposed, the package including a first package portion and a second package portion movably mounted relative to each other between a storage configuration in which the first and second package portions prevent a removal of the pre-filled syringe out from the package, and an opening configuration in which the first and second package portions enable an at least partial removal of the pre-filled syringe out from the package, the medical device being configured such that a displacement of the first and second package portions from the storage configuration to the opening configuration causes a displacement of the piston of the pre-filled syringe from a first piston position to a second piston position.

Such a configuration of the medical device according to the present invention ensures an activation of the pre-filled syringe prior to its removal out from the package, and therefore ensures a reliable and non-dangerous administration of the fluid to be administrated contained in the pre-filled syringe.

In particular, such a configuration of the medical device according to the present invention simplifies the step of preparing the syringe and therefore ensures saving time in an emergency situation. Thus, the medical device according to the present invention greatly limits the risk of injury to hospital staff and the risk of dosage error, in particular in emergency situation.

The medical device may further have one or more of the following features, considered separately or in combination.

According to an embodiment of the invention, the package is elongated and extends in an extension direction.

According to an embodiment of the invention, the first package portion includes a receiving housing in which the pre-filled syringe is at least partially disposed, and a passage opening emerging into the receiving housing and intended for the passage of the pre-filled syringe, the second package portion being configured to at least partially close the passage opening and to prevent a removal of the pre-filled syringe out from the receiving housing when the first and second package portions are in the storage configuration, and being configured to at least partially clear the passage opening and to enable a removal of the pre-filled syringe out from the receiving housing when the first and second package portions are in the opening configuration.

According to an embodiment of the invention, the first and second package portions are configured to occupy an intermediate activation configuration, the package being configured such that a displacement of the first and second package portions from the storage configuration to the intermediate activation configuration causes a displacement of the piston in the syringe body in a first axial direction.

According to an embodiment of the invention, the package is configured such that a displacement of the first and second package portions from the intermediate activation configuration to the opening configuration causes a displacement of the piston in the syringe body in a second axial direction opposite to the first axial direction.

According to an embodiment of the invention, the package is configured such that a displacement of the first and second package portions from the intermediate activation configuration to the opening configuration causes a displacement of the piston from the second piston position to the first piston position.

According to an embodiment of the invention, one of the first and second package portions includes a first axial thrust surface configured to transmit a thrust force to the piston, and the other of the first and second package portions includes a second axial thrust surface configured to transmit a thrust force to the syringe body, the package being configured such that a displacement of the first and second package portions from the storage configuration to the intermediate activation configuration causes bringing the first and second axial thrust surfaces together axially so as to result in a relative displacement of the syringe body and the piston.

According to an embodiment of the invention, the package is configured such that a displacement of the first and second package portions from the intermediate activation configuration to the opening configuration causes an axial separation of the first and second axial thrust surfaces.

According to an embodiment of the invention, the pre-filled syringe includes a piston rod secured in translation with the piston and movably mounted relative to the syringe body in the axial direction of displacement, and one of the first and second package portions is configured to cooperate with the piston rod and displace the piston rod in the axial direction of displacement during the displacement of the first and second package portions from the storage configuration to the opening configuration.

According to an embodiment of the invention, the first axial thrust surface is configured to transmit a thrust force to the piston rod.

According to an embodiment of the invention, the first package portion includes at least one retaining member configured to retain the pre-filled syringe on the first package part. These arrangements allow in particular being able to aseptically present the pre-filled syringe to a user, and helping the user to grasp it while maintaining an asepsis.

According to an embodiment of the invention, the at least one retaining member is configured to cooperate with the piston rod or the syringe body.

According to an embodiment of the invention, the at least one retaining member is configured to displace the piston rod at a distance from the syringe body when the first and second package portions are displaced from the intermediate activation configuration to the opening configuration, so as to displace the piston from the first piston position to the second piston position.

According to an embodiment of the invention, the pre-filled syringe includes a connecting tip including a tubular connecting portion intended for the passage of the fluid to be administrated, and an obturator configured to close a free end of the tubular connecting part, the obturator being connected to the free end of the tubular connecting portion by a frangible area.

According to an embodiment of the invention, the pre-filled syringe includes a protective cap mounted on the connecting tip.

According to an embodiment of the invention, the protective cap comprises a coupling portion coupled to the obturator such that a rotation of the coupling portion about an axis of rotation parallel to the extension direction of the tubular connecting portion causes a breakage of the frangible area.

According to an embodiment of the invention, the second package portion includes at least one retaining element configured to retain the protective cap, the package being configured such that a displacement of the first and second package portions from the storage configuration to the opening configuration causes a retention of the protective cap on the second package portion by the at least one retaining element and a breakage of the frangible area connecting the obturator and the tubular connecting portion. In particular, the retention of the protective cap by the at least one retaining element during the displacement of the first and second package portions from the storage configuration to the opening configuration induces the breakage of the frangible area connecting the obturator and the tubular connecting portion.

According to an embodiment of the invention, the syringe body is secured in rotation with the first package portion.

According to an embodiment of the invention, the protective cap includes at least one drive element configured to cooperate with the at least one retaining element, the second package portion and the protective cap being mounted movable in rotation relative to each other such that the at least one retaining element is capable of occupying a first angular position in which the at least one retaining element is angularly offset from the at least one drive element, and a second angular position in which the at least one retaining element cooperates with the at least one drive element so as to break the frangible area and retain the protective cap, the package being configured such that a displacement of the first and second package portions from the storage configuration to the opening configuration causes a displacement of the at least one retaining member from the first angular position to the second angular position.

According to an embodiment of the invention, the drive element is a drive fin or rib, and may for example extend substantially longitudinally.

According to an embodiment of the invention, the at least one retaining element includes a radial stop surface configured to limit the angular travel of the at least one retaining element relative to the protective cap, and an axial stop surface configured to retain the protective cap on the second package portion.

According to an embodiment of the invention, the second package portion comprises two diametrically opposed retaining elements, and the protective cap includes two diametrically opposite drive elements each configured to cooperate with a respective one of the two retaining elements. Advantageously, the two retaining elements form a bayonet retaining system.

According to an embodiment of the invention, the package includes guide means configured to guide one of the first and second package portions relative to the other of the first and second package portions according to a first helical movement in a first winding direction during a displacement of the first and second package portions from the storage configuration to the intermediate activation configuration, and according to a second helical movement in a second winding direction reversed with respect to the first winding direction during a displacement of the first and second package portions from the intermediate activation configuration to the opening configuration.

According to an embodiment of the invention, the guide means include a guide lug provided on one of the first and second package portions, and a guide groove provided on the other of the first and second package portions, the guide lug being slidably mounted in the guide groove.

According to an embodiment of the invention, the guide groove includes a first groove portion helically wound in a first winding direction, and a second groove portion helically wound in a second winding direction reversed with respect to the first winding direction. Advantageously, the second groove portion extends in the extension of the first groove portion.

According to an embodiment of the invention, the guide groove includes a third groove portion configured to enable a removal of the guide lug out from the guide groove. These arrangements enable a removable mounting of one of the first and second package portions on the other of the first and second package portions.

According to an embodiment of the invention, the third groove portion is rectilinear and extends substantially parallel to the extension direction of the pre-filled syringe, and more particularly of the package.

According to an embodiment of the invention, the first and second package portions are pivotally mounted relative to each other about a pivot axis between the storage configuration and the opening configuration.

According to an embodiment of the invention, the second package portion includes an actuating member including a cam surface configured to displace the piston rod from a first rod position to a second rod position during the pivoting of the first and second package portions from the storage configuration to the opening configuration.

According to an embodiment of the invention, the first package portion includes immobilizing means configured to axially immobilize the syringe body on the first package portion.

According to an embodiment of the invention, the immobilizing means include at least one first axial stop surface and a second axial stop surface disposed on either side of a bearing collar provided on the syringe body, and for example on a proximal end portion of the syringe body.

According to an embodiment of the invention, at least one of the first and second package portions includes gripping means, such as notches, configured to facilitate the displacement of the first and second package portions from the storage configuration to the opening configuration.

According to an embodiment of the invention, the package includes locking means movable between a locking position in which the locking means prevent a displacement of the first and second package portions from the storage configuration to the opening configuration, and an unlocking position in which the locking means enable a displacement of the first and second package portions from the storage configuration to the opening configuration.

According to an embodiment of the invention, the locking means comprise a locking housing provided on one of the first and second package portions, and at least one locking tab provided on the other of the first and second package portions and provided with a locking element, the locking tab being elastically deformable between a locking position in which the locking element is configured to cooperate with the locking housing and an unlocking position in which the locking element is configured to release the locking housing.

According to an embodiment of the invention, the first package portion includes at least one biasing member configured to bias the piston rod towards the first rod position. Advantageously, the at least one biasing member is elastically deformable. The at least one biasing member may for example be integral with the first package portion.

According to an embodiment of the invention, the package includes at least one blocking member configured to prevent a displacement of the first and second package portions from the opening configuration to the storage configuration. Such a configuration allows indicating to a user whether or not the package has already been opened, and therefore guaranteeing the sterility of the pre-filled syringe disposed in the package to a user.

The at least one blocking element is, for example, an elastically deformable blocking leg between a release position in which the blocking leg enables a displacement of the first and second package portions from the storage configuration to the opening configuration, and a blocking position in which the blocking leg prevents a displacement of the first and second package portions from the opening configuration to the storage configuration.

According to an embodiment of the invention, the second package portion is removably mounted on the first package portion.

According to an embodiment of the invention, the medical device includes a desiccant and/or an oxygen absorber disposed in the package.

According to an embodiment of the invention, the package includes a hooking opening intended for the passage of a support member of a showcase for medical devices.

According to an embodiment of the invention, the pre-filled syringe is disposed in a sterile manner in the package. Therefore, the pre-filled syringe can be manipulated in an aseptic care environment.

According to an embodiment of the invention, the pre-filled syringe is made of synthetic material. Advantageously, the pre-filled syringe is obtained by molding, and the obturator is molded integrally with the connecting tip and the syringe body.

According to an embodiment of the invention, the connecting tip is of the Luer or Luer-Lock type.

According to an embodiment of the invention, the protective cap is fastened on the obturator, in particular by welding, gluing or mechanical interference.

According to an embodiment of the invention, the medical device includes at least one communication element, such as an RFID tag or an NFC tag, configured to cooperate with a communication device, such as a smartphone, a terminal, etc.

According to an embodiment of the invention, the package may be provided with an identification code allowing identifying the pre-filled syringe disposed in the package. The identification code may for example be disposed on a label, and be in the form of a barcode or datamatrix code, or indicate the name of the fluid to be administered contained in the pre-filled syringe. These arrangements allow avoiding the administration errors by the healthcare staff.

According to an embodiment of the invention, the package has a non-circular, and for example rectangular, square or ellipsoidal cross-section. These arrangements avoid the rolling of the package on a horizontal support.

According to an embodiment of the invention, the package includes at least two lateral bearing surfaces which are substantially planar and opposite to each other. These arrangements allow in particular a stacking of different medical devices according to the present invention, which reduces the storage space of these devices in the medicine storage areas, such as in the medicine cabinets of the offices of the care staff.

According to an embodiment of the invention, the package is rigid. These arrangements provide the package with high puncture and impact resistance, and thus ensures a greatly improved protection of the pre-filled syringe. In addition, such a configuration of the package allows disposing the pre-filled syringe after use at least partly in the package, and therefore facilitating its disposal.

According to an embodiment of the invention, the package is opaque, that is to say that it does not allow light to pass therethrough. These arrangements ensure a protection of the pre-filled syringe against the light radiation during the storage of the medical device.

According to an embodiment of the invention, the medical device includes a piston rod removably mounted on the package, the piston rod being configured to be connected to the piston after removal of the pre-filled syringe out from the package and to displace the piston in the axial direction of displacement.

According to an embodiment of the invention, the medical device includes at least one injection needle removably mounted on the package.

According to an embodiment of the invention, in the storage configuration, the first and second package portions are assembled to each other so as to form a barrier, and in particular so as to form a barrier against microorganisms and gases.

According to an embodiment of the invention, at least one, and for example each, of the first and second package portions is provided with at least one passage orifice intended for the passage of a sterilization fluid, such as water vapor or ethylene oxide. Advantageously, the at least one passage orifice is covered by a film which is permeable to the sterilization fluid and impermeable to bacteria, such as a TYVEK film (trademark). In this manner, the medical device according to the present invention can be sterilized at the terminal phase, that is to say at the end of the assembly method.

According to an embodiment of the invention, the package includes first assembly means and second assembly means complementary to the first assembly means, the first assembly means of the medical device being configured to cooperate with the second assembly means of an adjacent medical device so as to allow the assembly of the two medical devices. These arrangements facilitate the storage of the medical devices and further reduces the storage space of these devices in the medicine storage areas.

According to an embodiment of the invention, the first assembly means are disposed opposite the second assembly means.

According to an embodiment of the invention, the first package portion is connected to the piston. For example, the first package portion may include a connecting portion connected to the piston, directly or via the piston rod, and extending at least partially in the syringe body.

According to an embodiment of the invention, the connecting portion and the piston are formed in one-piece. Nevertheless, the connecting portion may be fastened on the piston in particular by screwing, gluing or welding.

BRIEF DESCRIPTION OF THE DRAWINGS

In any case, the invention will be better understood using the following description with reference to the appended schematic drawings representing, as non-limiting examples, several embodiments of this medical device.

FIG. 1 is a perspective view of a medical device according to a first embodiment of the invention.

FIG. 2 is a perspective view cut along a longitudinal plane of the medical device of FIG. 1.

FIG. 3 is an exploded perspective view of the medical device of FIG. 1.

FIGS. 4 to 6 are perspective views cut along transverse planes of the medical device of FIG. 1, showing first and second package portions of the medical device in different relative angular positions.

FIG. 7 is a perspective view of the medical device of FIG. 1 in an opening configuration.

FIG. 8 is a perspective view cut along a longitudinal plane of the medical device of FIG. 1 in an intermediate activation configuration.

FIG. 9 is a perspective view of a medical device according to a second embodiment of the invention.

FIG. 10 is a perspective view of the medical device of FIG. 9, showing the first and second package portions of the medical device in an opening configuration.

FIG. 11 is a perspective view cut along a longitudinal plane of the medical device of FIG. 9.

FIG. 12 is a perspective view of a medical device according to a third embodiment of the invention.

DETAILED DESCRIPTION

Figure 13:
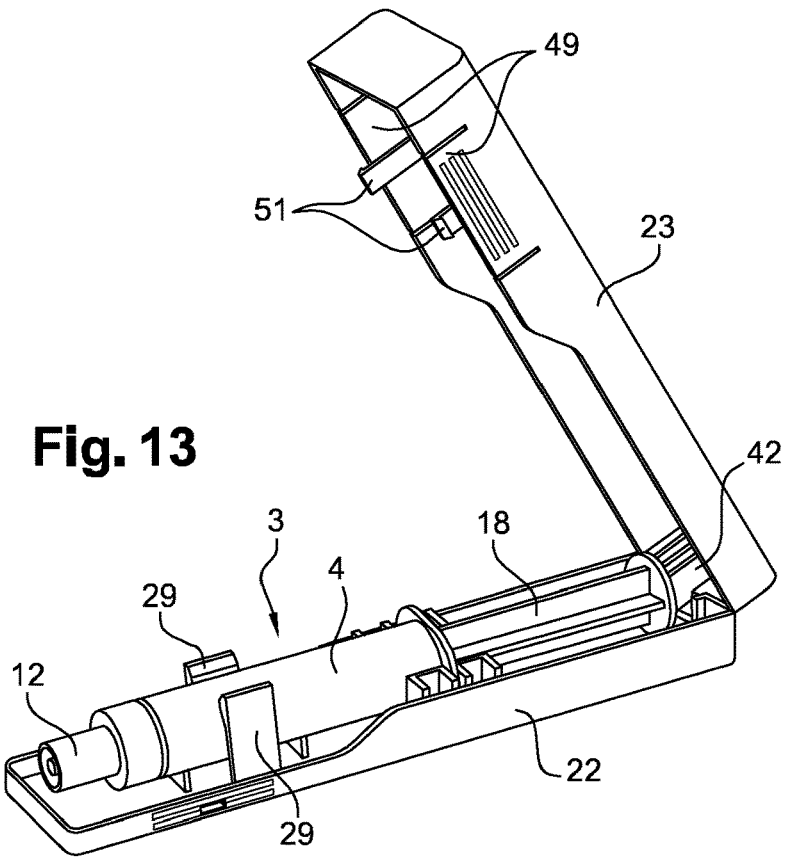
FIG. 13 is a perspective view of the medical device of FIG. 12, showing the first and second package portions of such a medical device in an opening configuration.
Figure 14:
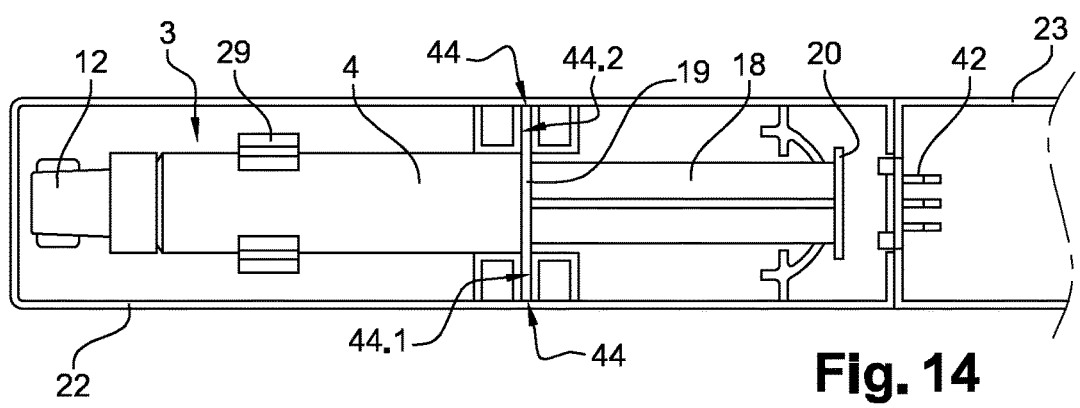
FIG. 14 is a partial top view of the medical device of FIG. 12.
Figure 15:
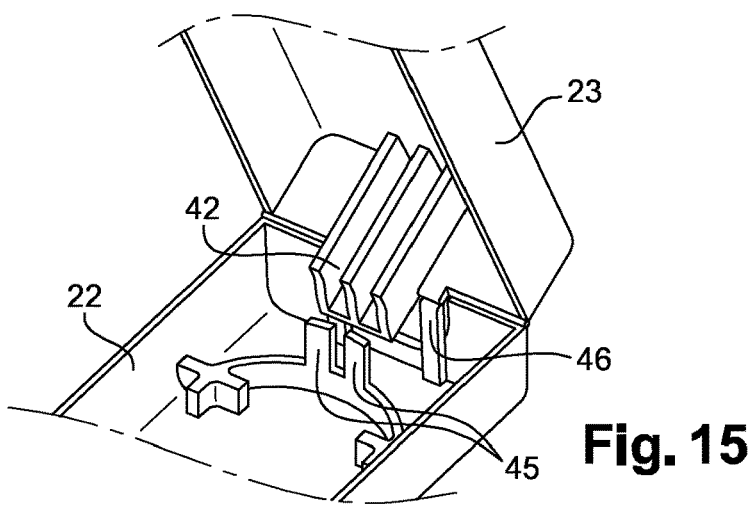
FIG. 15 is a partial perspective view, on an enlarged scale, of the medical device of FIG. 12.
Figure 16:
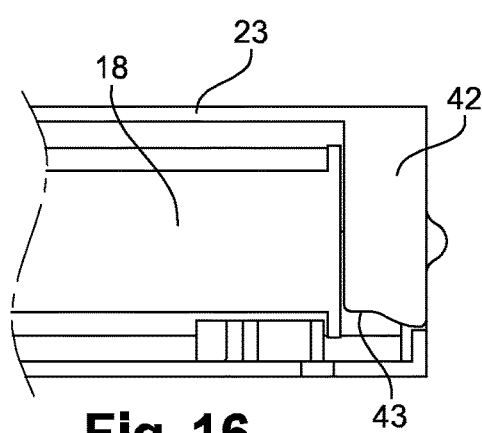
FIGS. 16 to 18 are partial sectional views of the medical device of FIG. 12, showing the package of such a medical device in different positions.
Figure 17:
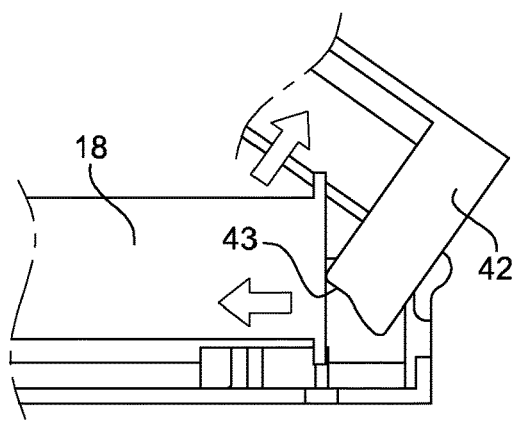
Figure 18:
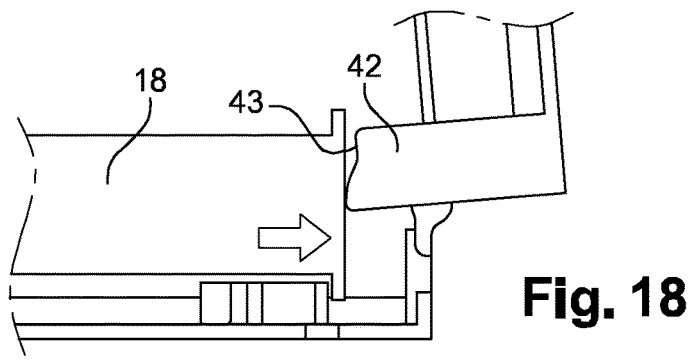
Figure 19:
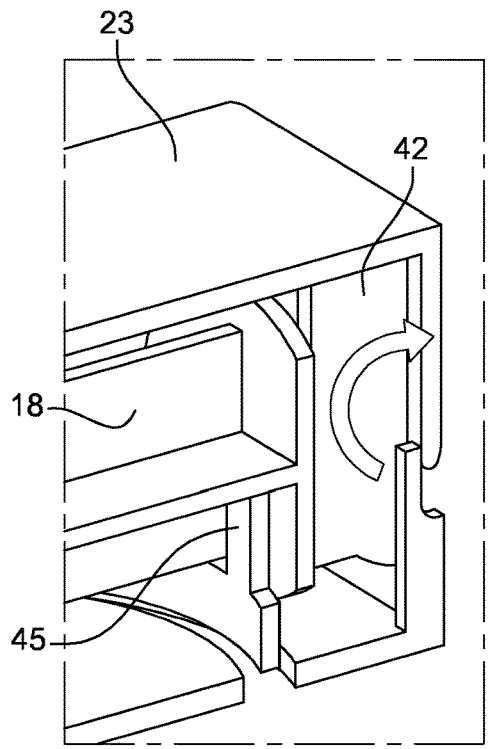
FIGS. 19 and 20 are partial perspective views cut along longitudinal planes of the medical device of FIG. 12, showing the package of such a medical device in different positions.
Figure 20:
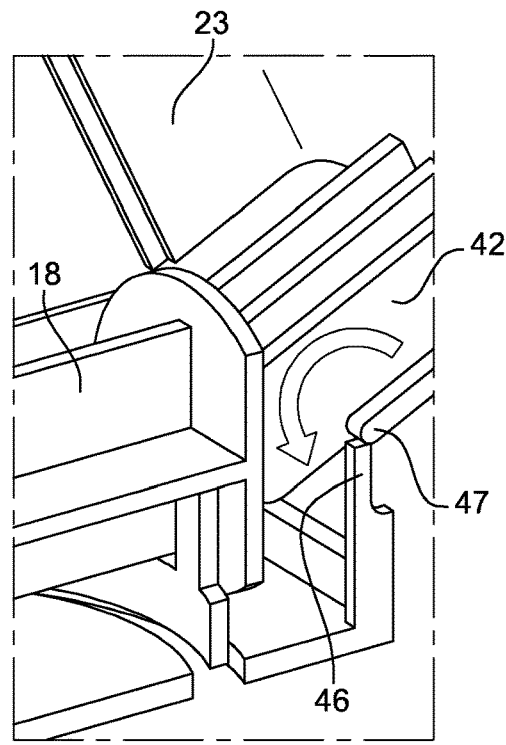
Figure 21:
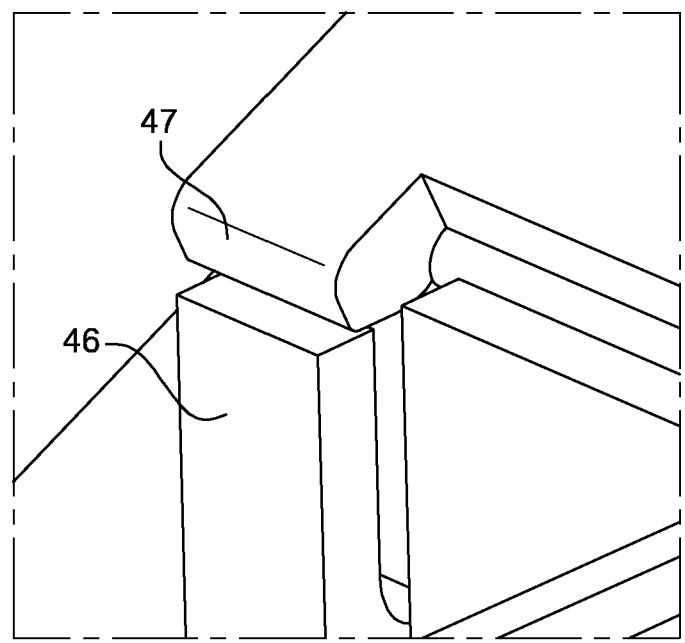
FIG. 21 is a view on an enlarged scale of a detail of FIG. 18.

FIGS. 1 to 8 represent a medical device 2 according to a first embodiment of the invention.

As shown more particularly in FIGS. 2 and 3, the medical device 2 includes a pre-filled syringe 3 including a tubular syringe body 4 and with a generally cylindrical shape. The syringe body 4 includes a proximal end 4.1 and a distal end 4.2.

The pre-filled syringe 3 also includes a Luer-lock type connecting tip 5 disposed at the level of the distal end 4.2 of the syringe body 4. The connecting tip 5 comprises a tubular connecting portion 6 fluidly connected to the internal volume of the syringe body 4, and a locking sleeve 7 coaxially disposed at the tubular connecting portion 6 and surrounding the latter. The locking sleeve 7 preferably includes an internal thread 8.

The pre-filled syringe 3 further includes an obturator 9 connected by a frangible area 11 at the free end of the connecting portion 6. The frangible area 11 between the connecting portion 6 and the obturator 9 is advantageously made by an annular thinning of the material along the connecting line between the free end of the connecting portion 6 and the obturator 9. Such a configuration of the frangible area 11 enables an easy separation of the obturator 9 and the connecting portion 6.

The syringe body 4, the connecting tip 5 and the obturator 9 are for example made of synthetic material and in an integral part by molding.

The pre-filled syringe 3 further includes a protective cap 12 removably mounted on the connecting tip 5 in order to preserve the sterility of the connecting tip 5. The protective cap 12 advantageously includes a mounting portion 13 configured to cooperate with the external surface of the locking sleeve 7. The mounting portion 13 preferably extends to the vicinity of the syringe body 4, and advantageously has an outer diameter substantially corresponding to the outer diameter of the syringe body 4.

The protective cap 12 also comprises a coupling portion 14 secured to the mounting portion 13. According to the embodiment represented in FIGS. 1 to 8, the coupling portion 14 includes a coupling housing 15 emerging into an inner volume delimited by the mounting portion 13. The coupling housing 15 is arranged to cooperate with the obturator 9 such that the rotation of the coupling portion 14 about an axis of rotation coinciding with the extension axis of the connecting portion 6 drives in rotation the obturator 9 and results in the breakage of the frangible area 11.

According to the embodiment represented in FIGS. 1 to 8, each of the obturator 9 and the coupling housing 15 has a frustoconical shape. These arrangements enable a forced fitting of the obturator 9 in the coupling housing 15 such that, after breakage of the frangible area 11, the obturator 9 is held in the coupling housing 15 and cannot fall to the ground. According to another embodiment of the invention, the obturator 9 and the coupling housing 15 might have other shapes, such as complementary polygonal shapes, for example hexagonal shapes.

The pre-filled syringe 3 also includes a piston 16 slidably mounted inside the syringe body 4 along the longitudinal axis thereof. The syringe body 4 and the piston 16 thus delimit an inner chamber 17 containing a fluid to be administered to a patient, for example a drug solution.

The pre-filled syringe 3 further includes a piston rod 18, forming a plunger, movably relative to the syringe body 4 according to an axial direction of displacement. The piston rod 18 is connected to the piston 16, and is secured in translation with the piston 16. The outer surface of the syringe body 4 advantageously includes a bearing collar 19 located at the level of the proximal end 4.1 of the syringe body 4, and on which the user's fingers press when a thrust is exerted by the latter on a bearing portion 20 provided at the end of the piston rod 18 opposite to the piston 16.

The medical device 2 further includes a package 21 in which the pre-filled syringe 3 is disposed, preferably in a sterile manner. Advantageously, the package 21 is elongated and extends in an extension direction.

The package 21 includes more particularly a first package portion 22 and a second package portion 23. The first and second package portions 22, 23 are advantageously rigid and opaque, and may be made for example of plastic material.

The first package portion 22 includes a gripping portion 24 with a generally tubular shape, and a mounting portion 25 also with a generally tubular shape and extending coaxially to the gripping portion 24. The gripping portion 24 and the mounting portion 25 delimit a receiving housing 26 in which the piston rod 18 and a portion of the syringe body 4 are disposed.

The mounting portion 25 includes a passage opening 27 emerging into the receiving housing 26, and intended for the passage of the piston rod 18 and the syringe body 4 in order to enable their insertion and removal into and out from the receiving housing 26.

The gripping portion 24 includes an axial thrust surface 28 partially delimiting the receiving housing 26, and on which the bearing portion 20 of the piston rod 18 bears. The axial thrust surface 28 is more particularly configured to transmit a thrust force to the piston rod 18.

According to the first embodiment of the invention, the first package portion 22 also includes a plurality of retaining members 29 configured to cooperate with the bearing collar 19 of the syringe body 4 so as to retain the syringe body 4 on the first package portion 22. Each retaining member 29 is advantageously in the form of an elastically deformable retaining finger, and preferably extends parallel to the extension direction of the syringe body 4. Each retaining member 29 extends for example at a distance from and along the internal surface of the mounting portion 25.

It should be noted that the first package portion 22 is configured such that the syringe body 4 is secured in rotation with the first package portion 22.

The second package portion 23 also includes a gripping portion 31 with a generally tubular shape, and a mounting portion 32 also with a generally tubular shape. The gripping portion 31 and the mounting portion 32 delimit an inner housing 33 in which the protective cap 12 and a portion of the syringe body 4 are disposed.

The mounting portion 32 includes a passage opening 34 emerging into the inner housing 33, and intended for the passage of the protective cap 12 and the syringe body 4 in order to enable their insertion and removal into and out from the inner housing 33. The mounting portion 32 is configured to cooperate with the mounting portion 25 of the first package portion 22, and more particularly to cooperate with the internal surface of the mounting portion 25.

The gripping portion 31 includes more particularly an axial thrust surface 35 on which the protective cap 12 bears. The axial thrust surface 35 is more particularly configured to transmit a thrust force to the syringe body 4 via the protective cap 12.

As shown in particular in FIGS. 4 to 6, the first and second package portions 22, 23 are movably mounted relative to each other, and are capable of occupying in particular:
- a storage configuration (see FIGS. 1 and 4) in which the first and second package portions 22, 23 prevent a removal of the pre-filled syringe 3 out from the package 21,
- an intermediate activation configuration (see FIGS. 5 and 8) in which the piston 16 is activated,
- an intermediate breaking configuration (see FIG. 6) in which the frangible area 11 is broken, and
- an opening configuration (see FIG. 7) in which the first and second package portions 22, 23 enable a removal of the pre-filled syringe 3 out from the package 21.

The package 21 includes guide means configured to guide the first package portion 22 relative to the second package portion 23:
- according to a first helical movement in a first winding direction during the displacement of the first and second package portions 22, 23 from the storage configuration to the intermediate activation configuration,
- according to a second helical movement in a second winding direction reversed with respect to the first winding direction during the displacement of the first and second package portions 22, 23 from the intermediate activation configuration to the intermediate breaking configuration, and according to an axial movement during the displacement of the first and second package portions 22, 23 from the intermediate breaking configuration to the opening configuration.

The guide means include more particularly a guide groove 36 provided on the external surface of the mounting portion 31 of the second package portion 23, and a guide lug 37 provided on the internal surface of the mounting portion 25 of the first package portion 22 and slidably mounted in the guide groove 36. The guide groove 36 includes a first groove portion 36.1 helically wound in a first winding direction, and a second groove portion 36.2 extending in the extension of the first groove portion 63.1 and being helically wound in a second winding direction reversed with respect to the first winding direction.

Advantageously, the guide groove 36 includes a third groove portion 36.3 extending parallel to the extension direction of the second package portion 23 and emerging at the level of the free end of the mounting portion 31. The third groove portion 36.3 is more particularly configured to enable a removal of the guide lug 37 out from the guide groove 36, so as to enable a separation of the first and second package portions 22, 23.

The package 21 is configured such that a displacement of the first and second package portions 22, 23 from the storage configuration to the intermediate activation configuration causes bringing the first and second axial thrust surfaces 28, 35 together, and therefore bringing the bearing portion 20 and the bearing collar 19 together. Thus, the package 21 is more particularly configured such that a displacement of the first and second package portions 22, 23 from the storage configuration to the intermediate activation configuration causes a displacement of the piston 16 in the syringe body 4 in the direction of the protective cap 12, and from a first piston position, called rest position, to a second piston position, called activated position. Such a configuration of the medical device 2 according to the first embodiment of the invention thus guarantees an activation of the pre-filled syringe 3 before its removal from the package 21, and thus ensures a reliable and painless administration of the fluid contained in the inner chamber 17 of the pre-filled syringe 3.

It should be noted that a displacement of the first and second package portions 22, 23 from the intermediate activation configuration to the opening configuration causes an axial separation of the first and second axial thrust surfaces 28, 35.

Advantageously, as shown in FIGS. 2 and 4 to 6, the second package portion 23 includes two retaining elements 38 disposed in the inner housing 33 and extending from the internal surface of the gripping portion 31. Advantageously, the two retaining elements 38 are diametrically opposite, and forms a bayonet retaining system. Thus, each retaining element 38 includes a radial stop surface 38.1 and an axial stop surface 38.2.

The protective cap 12 further includes two diametrically opposite drive elements 39, and configured to cooperate each with a respective one of the two retaining elements 38. Advantageously, each drive element 38 is in the form of a drive fin or rib, and extends parallel to the extension direction of the pre-filled syringe 3.

As shown more particularly in FIGS. 4 to 6, the second package portion 23 and the protective cap 12 are mounted movable in rotation relative to each other such that each retaining element 38 is capable of occupying a first angular position in which said retaining element 38 is angularly offset from the respective driving element 39, and a second angular position in which said retaining element 38 cooperates with the respective drive element 39, and more specifically with the respective radial stop surface 38.1 which is configured to limit the angular travel of said retaining element 38 relative to the protective cap 12 and the respective axial stop surface 38.2 which is configured to retain the protective cap 12.

Thus, the package 21 is also configured such that a displacement of the first and second package portions 22, 23 from the storage configuration to the opening configuration causes a displacement of the retaining elements 38 from their first angular position to their second angular position, and more specifically, a breakage of the frangible area 11 connecting the obturator 9 and the tubular connecting portion 6 and a retention of the protective cap 12 on the second package portion 23. These arrangements allow ensuring a removal of the protective cap 12 from the connecting tip 5 and a breakage of the frangible area 11 before the removal of the pre-filled syringe 3 out from the package 21. This results in a facilitated gesture for the practitioner.

It should be noted that the retaining elements 38 are positioned such that breakage of the frangible area 11 occurs after the activation of the piston 16, and therefore during the displacement of the first and second package portions 22, 23 from the intermediate activation configuration to the opening configuration.

According to the first embodiment represented in FIGS. 1 to 8, the first package portion 22 advantageously includes two lateral bearing surfaces 41 which are substantially planar and opposite to each other. These arrangements allow, on the one hand, avoiding a rolling of the package 21 on a horizontal support, and on the other hand, ensuring an easy stacking of different medical devices 2 according to the first embodiment, which reduces the storage space of these devices in the medicine storage areas, such as in the medicine cabinets of the offices of the care staff.

It should also be noted that the first package portion 22 might be provided with one or several passage orifice(s) emerging into the receiving housing 26 and intended for the passage of a sterilization fluid, such as water vapor or ethylene oxide. Similarly, the second package portion 23 might be provided with one or several passage orifice(s) emerging into the inner housing 33 and intended for the passage of a sterilization fluid. Advantageously, each passage orifice might be covered by a film which is permeable to the sterilization fluid and impermeable to bacteria, such as a TYVEK film (trademark).

FIGS. 9 to 11 represent a medical device 2 according to a second embodiment which differs from the first embodiment essentially in that the retaining members 29 are configured to cooperate with the bearing portion 20 of the piston rod 18, and to axially displace the piston rod 18 at a distance from the syringe body 4 when the first and second package portions 22, 23 are displaced from the intermediate activation configuration to the opening configuration.

The package 21 is more specifically configured such that a displacement of the first and second package portions 22, 23 from the intermediate activation configuration to the opening configuration causes a displacement of the piston 16 from the second piston position to the first piston position. These arrangements allow repositioning the piston 16 in its rest position, and therefore avoiding an expulsion of fluid out from the pre-filled syringe 3 during the breakage of the frangible area 11.

Furthermore, according to the second embodiment of the invention, the package 21 has a rectangular section.

FIGS. 12 to 21 represent a medical device 2 according to a third embodiment which differs from the first embodiment essentially in that the first and second package portions 22, 23 are pivotally mounted relative to each other about a pivot axis transverse to the extension direction of the package 21, and in that the second package portion 23 includes an actuating member 42 including a cam surface 43 configured to displace the piston rod 18 from a first rod position (see FIG. 16) to a second rod position (see FIG. 17) during the pivoting of the first and second package portions 22,23 from the storage configuration to the intermediate activation configuration.

According to this third embodiment, the first package portion 22 includes immobilizing means configured to axially immobilize the syringe body 4 on the first package portion 22. Advantageously, the immobilizing means include two immobilizing grooves 44 disposed on either side of the pre-filled syringe 3 and in which the bearing collar 19 of the syringe body 4 is received. Each immobilizing groove 44 is delimited by a first axial stop surface 44.1 and a second axial stop surface 44.2 disposed on either side of the bearing collar 19. Such immobilizing means allow ensuring a relative displacement of the piston rod 18, and therefore of the piston 16, relative to the syringe body 4 during the displacement of the first and second package portions 22, 23 from the storage configuration to the intermediate activation configuration.

According to this third embodiment, the first package portion 22 also includes one or several biasing member(s) 45 (see FIG. 15) configured to bias the piston rod 18 towards the first rod position during the pivoting of the first and second package portions 22, 23 from the intermediate activation configuration to the opening configuration. These arrangements allow ensuring a repositioning of the piston 16 in the first piston position after the displacement of the first and second package portions 22, 23 in their opening configuration.

Advantageously, the or each biasing member 45 is elastically deformable, and may be in the form of a biasing leg adapted to cooperate with the bearing portion 20 of the piston rod 18.

According to this third embodiment, the package 21 further includes a blocking element 46 (see in particular FIGS. 19 to 21) configured to prevent a displacement of the first and second package portions 22, 23 from the opening configuration to the storage configuration. Such a configuration allows guaranteeing, to a user, the sterility of the pre-filled syringe 3 of a medical device 2 according to the third embodiment of the invention.

For example, the blocking element 46 may be provided on the first package portion 22 and be in the form of an elastically deformable blocking leg between a release position in which the blocking leg enables a displacement of the first and second package portions 22, 23 from the storage configuration to the opening configuration, and a blocking position (see FIGS. 20 and 21) in which the blocking leg prevents a displacement of the first and second package portions 22, 23 from the opening configuration to the storage configuration. Advantageously, the blocking element 46 is configured to cooperate with a blocking lug 47 provided on the second package portion 23.

Advantageously, the package 21 further includes locking means movable between a locking position (see FIG. 12) in which the locking means prevent a displacement of the first and second package portions 22, 23 from the storage configuration to the opening configuration, and an unlocking position in which the locking means enable a displacement of the first and second portions 22, 23 from the storage configuration to the opening configuration.

The locking means include for example at least one locking housing 48 provided on the first package portion 22, and at least one locking tab 49 provided on the second package portion 23 and provided with a locking element 51. The or each locking tab 49 is elastically deformable between a locking position in which the respective locking member 51 is configured to cooperate with the respective locking housing 48, and an unlocking position in which the respective locking element 51 is configured to release the respective locking housing 48. Preferably, a user can deform the or each locking tab 49 towards its unlocking position by exerting a pressure on said locking tab 49.

It should be noted that, according to the third embodiment of the invention, the package 21 is not configured such that a displacement of the first and second package portions 22, 23 causes a breakage of the frangible area 11 and the removal of the protective cap 12. Thus, according to this embodiment, the practitioner will have to displace the protective cap 12 in rotation relative to the syringe body 4, using the drive members 39, in order to break the frangible area 11 and remove the protective cap 12.

Figure 22:
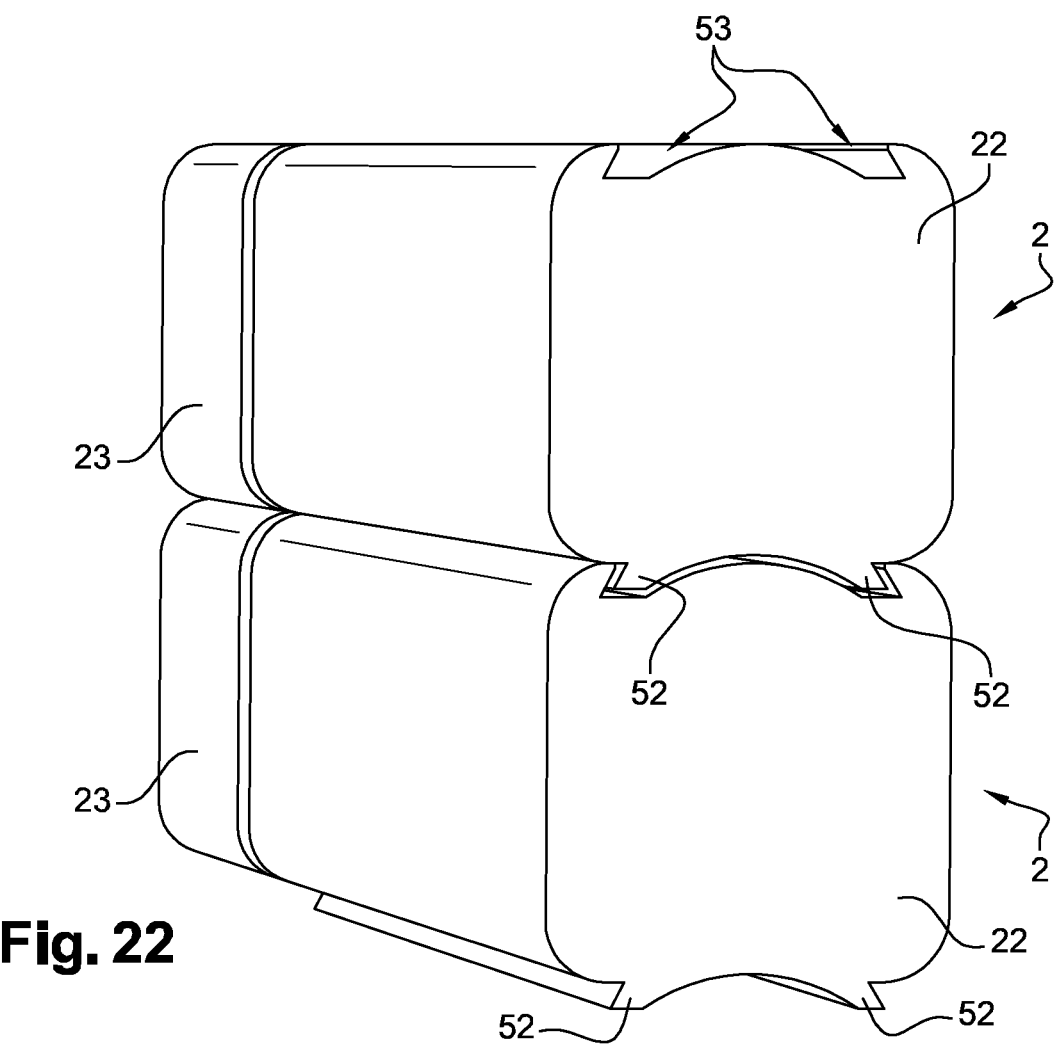
FIG. 22 is a perspective view of two medical devices according to a fourth embodiment of the invention.

FIG. 22 represents medical devices 2 according to a fourth embodiment of the invention which differs from the first embodiment essentially in that each package 21 includes first assembly means and second assembly means complementary to the first assembly means and disposed opposite to the first assembly means, the first assembly means of a medical device 2 being configured to cooperate with the second assembly means of an adjacent medical device 2 so as to allow the assembly of the two adjacent medical devices.

The first and second assembly means might for example include respectively one or several assembly rib(s) 52 and one or several assembly groove(s) 53. Nevertheless, the first and second assembly means could take any other form, and for example include lugs or assembly tabs configured to cooperate with complementary assembly housings.

It should be noted that the first and second assembly means could be provided only on the first package portion 22, only on the second package portion 23, or else on the first and second package portions.

According to an embodiment of the invention not represented in the figures, the medical device 2 could comprise a desiccant and/or an oxygen absorber disposed in the package 21.

According to an embodiment of the invention not represented in the figures, the package 21 could include a hooking opening intended for the passage of a support member of a showcase for medical devices, thus allowing the arrangement of the package 21 on such a showcase.

According to an embodiment of the invention not represented in the figures, the medical device 2 could include a communication element, such as an RFID tag or an NFC tag, configured to cooperate with a communication device, such as a smartphone, a terminal, etc. The communication element is advantageously disposed on or in the package 21.

According to an embodiment of the invention, the package 21 could be provided with an identification code allowing identifying the pre-filled syringe 3 disposed in the package 21. The identification code could for example be disposed on a label, and be in the form of a barcode or a datamatrix code.

Of course, the invention is not limited to the sole embodiments of this medical device, described above as examples, it encompasses on the contrary all variants thereof.

The invention claimed is:

1. A medical device, comprising:
a pre-filled syringe including a syringe body and a piston slidably mounted in the syringe body in an axial direction of displacement, the syringe body and the piston delimiting an inner chamber containing a fluid to be administered to a patient, the pre-filled syringe further including a piston rod secured in translation with the piston and movably mounted relative to the syringe body in the axial direction of displacement; and
a package in which the pre-filled syringe is disposed, the package including a first package portion and a second package portion movably mounted relative to each other between a storage configuration in which the first and second package portions prevent a removal of the pre-filled syringe out from the package, and an opening configuration in which the first and second package portions enable an at least partial removal of the pre-filled syringe out from the package, one of the first and second package portions being configured to displace the piston rod with respect to the syringe body during a displacement of the first and second package portions from the storage configuration to the opening configuration, the medical device being configured such that the displacement of the first and second package portions from the storage configuration to the opening configuration causes a displacement of the piston of the pre-filled syringe with respect to the syringe body from a first piston position to a second piston position.

2. The medical device according to claim 1, wherein the first package portion includes a receiving housing in which the pre-filled syringe is at least partially disposed, and a passage opening emerging into the receiving housing and intended for the passage of the pre-filled syringe, the second package portion being configured to at least partially close the passage opening and to prevent a removal of the pre-filled syringe out from the receiving housing when the first and second package portions are in the storage configuration, and being configured to at least partially clear the passage opening and to enable a removal of the pre-filled syringe out from the receiving housing when the first and second package portions are in the opening configuration.

3. The medical device according to claim 1, wherein the first and second package portions are configured to occupy an intermediate activation configuration, the package being configured such that a displacement of the first and second package portions from the storage configuration to the intermediate activation configuration causes a displacement of the piston in the syringe body in a first axial direction.

4. The medical device according to claim 3, wherein the package is configured such that a displacement of the first and second package portions from the intermediate activation configuration to the opening configuration causes a displacement of the piston in the syringe body in a second axial direction opposite to the first axial direction.

5. The medical device according to claim 3, wherein one of the first and second package portions includes a first axial thrust surface configured to transmit a thrust force to the piston, and the other of the first and second package portions includes a second axial thrust surface configured to transmit a thrust force to the syringe body, the package being configured such that a displacement of the first and second package portions from the storage configuration to the intermediate activation configuration causes bringing the first and second axial thrust surfaces together axially so as to result in a relative displacement of the syringe body and the piston.

6. The medical device according to claim 1, wherein the first package portion includes at least one retaining member configured to retain the pre-filled syringe on the first package portion.

7. The medical device according to claim 1, wherein the pre-filled syringe includes a connecting tip including a tubular connecting portion intended for the passage of the fluid to be administrated, and an obturator configured to close a free end of the tubular connecting portion, the obturator being connected to the free end of the tubular connecting portion by a frangible area.

8. The medical device according to claim 7, wherein the pre-filled syringe includes a protective cap mounted on the connecting tip.

9. The medical device according to claim 8, wherein the protective cap comprises a coupling portion coupled to the obturator such that a rotation of the coupling portion about an axis of rotation parallel to an extension direction of the tubular connecting portion causes a breakage of the frangible area.

10. The medical device according to claim 9, wherein the second package portion includes at least one retaining element configured to retain the protective cap, the package being configured such that a displacement of the first and second package portions from the storage configuration to the opening configuration causes a breakage of the frangible area connecting the obturator and the tubular connecting portion and a retention of the protective cap on the second package portion.

11. The medical device according to claim 10, wherein the protective cap includes at least one drive element configured to cooperate with the at least one retaining element, the second package portion and the protective cap being mounted movable in rotation relative to each other such that the at least one retaining element is capable of occupying a first angular position in which the at least one retaining element is angularly offset from the at least one drive element, and a second angular position in which the at least one retaining element cooperates with the at least one drive element so as to break the frangible area and retain the protective cap, the package being configured such that a displacement of the first and second package portions from the storage configuration to the opening configuration causes a displacement of the at least one retaining element from the first angular position to the second angular position.

12. The medical device according to claim 3, wherein the package includes guide means configured to guide one of the first and second package portions relative to the other of the first and second package portions according to a first helical movement in a first winding direction during a displacement of the first and second package portions from the storage configuration to the intermediate activation configuration, and according to a second helical movement in a second winding direction reversed with respect to the first winding direction during a displacement of the first and second package portions from the intermediate activation configuration to the opening configuration.

13. The medical device according to claim 12, wherein the guide means include a guide lug provided on one of the first and second package portions, and a guide groove provided on the other of the first and second package portions, the guide lug being slidably mounted in the guide groove.

14. The medical device according to claim 1, wherein the first and second package portions are pivotally mounted relative to each other about a pivot axis between the storage configuration and the opening configuration, the second package portion including an actuating member including a cam surface configured to displace the piston rod from a first rod position to a second rod position during the pivoting of the first and second package portions from the storage configuration to the opening configuration.

15. The medical device according to claim 1, wherein the second package portion is removably mounted on the first package portion.

16. The medical device according to claim 1, which includes a desiccant and/or an oxygen absorber disposed in the package.

17. The medical device according to claim 1, wherein the pre-filled syringe is disposed in a sterile manner in the package.

18. The medical device according to claim 1, wherein the package includes first assembly means and second assembly means complementary to the first assembly means, the first assembly means of the medical device being configured to cooperate with the second assembly means of an adjacent medical device so as to allow the assembly of two medical devices.

19. The medical device according to claim 1, wherein said one of the first and second package portions is configured to displace the piston rod with respect to the syringe body and in the axial direction of displacement during the displacement of the first and second package portions from the storage configuration to the opening configuration, the medical device being configured such that the displacement of the first and second package portions from the storage configuration to the opening configuration causes the displacement of the piston of the pre-filled syringe with respect to the syringe body and in the axial direction of displacement.

20. A medical device, comprising:
   a pre-filled syringe including a syringe body and a piston slidably mounted in the syringe body in an axial direction of displacement, the syringe body and the piston delimiting an inner chamber containing a fluid to be administered to a patient; and
   a package in which the pre-filled syringe is disposed, the package including a first package portion and a second package portion movably mounted relative to each other between a storage configuration in which the first and second package portions prevent a removal of the pre-filled syringe out from the package, and an opening configuration in which the first and second package portions enable an at least partial removal of the pre-filled syringe out from the package, the medical device being configured such that a displacement of the first and second package portions from the storage configuration to the opening configuration causes a displacement of the piston of the pre-filled syringe from a first piston position to a second piston position,
   wherein the first and second package portions are configured to occupy an intermediate activation configuration, the package being configured such that a displacement of the first and second package portions from the storage configuration to the intermediate activation configuration causes a displacement of the piston in the syringe body in a first axial direction,
   wherein the package includes a guide assembly configured to guide one of the first and second package portions relative to the other of the first and second package portions according to a first helical movement in a first winding direction during a displacement of the first and second package portions from the storage configuration to the intermediate activation configuration, and according to a second helical movement in a second winding direction reversed with respect to the first winding direction during a displacement of the first and second package portions from the intermediate activation configuration to the opening configuration.

21. A medical device, comprising:
   a pre-filled syringe including a syringe body and a piston slidably mounted in the syringe body in an axial direction of displacement, the syringe body and the piston delimiting an inner chamber containing a fluid to be administered to a patient, the pre-filled syringe further includes a piston rod secured in translation with the piston and movably mounted relative to the syringe body in the axial direction of displacement; and
   a package in which the pre-filled syringe is disposed, the package including a first package portion and a second package portion pivotally mounted relative to each other about a pivot axis between a storage configuration in which the first and second package portions prevent a removal of the pre-filled syringe out from the package, and an opening configuration in which the first and second package portions enable an at least partial removal of the pre-filled syringe out from the package, the second package portion including an actuating member including a cam surface configured to displace the piston rod with respect to the syringe body from a first rod position to a second rod position during the pivoting of the first and second package portions from the storage configuration to the opening configuration, the medical device being configured such that a displacement of the first and second package portions from the storage configuration to the opening configuration causes a displacement of the piston of the pre-filled syringe from a first piston position to a second piston position.

* * * * *